(12) United States Patent
Rapp

(10) Patent No.: US 9,518,999 B2
(45) Date of Patent: Dec. 13, 2016

(54) INSTRUMENT AND PROCESS FOR THE STORING AND/OR PROCESSING OF LIQUID SAMPLES

(75) Inventor: Martin Rapp, Thalwil (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 587 days.

(21) Appl. No.: 13/236,863

(22) Filed: Sep. 20, 2011

(65) Prior Publication Data

US 2012/0244541 A1  Sep. 27, 2012

(30) Foreign Application Priority Data

Sep. 20, 2010  (EP) ..................................... 10177697

(51) Int. Cl.
| | | |
|---|---|---|
| *B01L 99/00* | (2010.01) | |
| *G01N 35/02* | (2006.01) | |
| *B01L 3/00* | (2006.01) | |
| *G01N 35/04* | (2006.01) | |
| *B65B 7/28* | (2006.01) | |

(52) U.S. Cl.
CPC ......... *G01N 35/028* (2013.01); *B01L 3/50853* (2013.01); *B01L 3/50851* (2013.01); *B01L 2200/0689* (2013.01); *B01L 2200/141* (2013.01); *B01L 2200/142* (2013.01); *B01L 2300/044* (2013.01); *B65B 7/2878* (2013.01); *G01N 2035/0405* (2013.01)

(58) Field of Classification Search
CPC ..................... G01N 35/00; G01N 2035/00277; G01N 2035/00306; G01N 2035/00346; G01N 2035/00495; G01N 35/028; B01L 3/50853; B01L 2200/0689; B01L 2300/044

USPC ................ 422/509, 547, 551, 560, 565, 567
See application file for complete search history.

(56) References Cited

U.S. PATENT DOCUMENTS

| | | | |
|---|---|---|---|
| 4,002,009 A | | 1/1977 | Tolosa et al. |
| 4,264,560 A | * | 4/1981 | Natelson ...................... 422/417 |
| 6,408,595 B1 | | 6/2002 | Friedman |
| 6,632,653 B1 | | 10/2003 | Astle |
| 7,445,752 B2 | | 11/2008 | Harms et al. |
| 2005/0226780 A1 | | 10/2005 | Sandell et al. |
| 2005/0232820 A1 | * | 10/2005 | Reed et al. ................... 422/100 |
| 2007/0014695 A1 | * | 1/2007 | Yue et al. ..................... 422/100 |
| 2008/0006202 A1 | | 1/2008 | Hirano et al. |
| 2008/0233586 A1 | | 9/2008 | Turner |

FOREIGN PATENT DOCUMENTS

| | | | | |
|---|---|---|---|---|
| DE | 10205977 A1 | | 8/2006 | |
| EP | 0 483 569 | * | 5/1992 | ............ B29C 65/16 |
| EP | 1 972 377 A2 | | 9/2008 | |
| JP | 2004-268980 | | 9/2004 | |

(Continued)

*Primary Examiner* — Jill Warden
*Assistant Examiner* — Dwayne K Handy
(74) *Attorney, Agent, or Firm* — Dinsmore & Shohl LLP

(57) ABSTRACT

An instrument and process for the automated storing and/or processing of liquid samples are disclosed. The instrument may comprise an instrument casing forming an internal space, a moving mechanism for moving at least one microplate for receiving the samples into and/or out of the internal space, and/or at least one rotatable sealing roller for pressing a sealing cover on the microplate while moving the microplate into or out of the internal space formed by the instrument casing.

17 Claims, 2 Drawing Sheets

(56) References Cited

FOREIGN PATENT DOCUMENTS

| WO | 00/66269 | 11/2000 |
| WO | 2005/028312 A1 | 3/2005 |
| WO | 2006/102297 A1 | 9/2006 |

\* cited by examiner

INSTRUMENT AND PROCESS FOR THE STORING AND/OR PROCESSING OF LIQUID SAMPLES

TECHNICAL FIELD

Embodiments of the present invention relate generally to the field of clinical analysis and medical diagnostics, and more particularly to an instrument and method for the automated storing and/or processing of liquid samples.

BACKGROUND

It is common practice to use integrally molded plastic disposables provided with a plurality of open-top wells sized to receive liquid samples for performing sample processing steps. Such disposables are commonly known as "microplates" or "multi-well plates". Several variations of microplates are well-known in the art.

A sealing cover may be applied to the top surface of the microplate to air-tightly seal the wells containing the liquid samples for various reasons. One reason is the necessity to avoid evaporation of liquids in order to ensure the integrity of the samples contained. Another reason is to prevent spilling of the samples during transport of the microplate from one location to another. Yet another reason is to prevent cross contamination of individual samples so as to provide a generally sterile and controlled environment under which the processing steps can be carried out. Conventionally, sealing of the microplates is done prior to charging the microplates into a processing device for processing the liquid samples.

Especially in quantitative PCR (PCR=polymerase chain reaction), it is convenient to use transparent sealing covers such as thin plastic foils which allow for an optical detection of reaction products even during progress of reactions. In practical use, for instance, a plastic foil provided with an adhesive backing is placed on top of the microplate wherein the adhesive backing faces the microplate. The plastic foil is pressed on the microplate, e.g., by means of a pressure roll rolling back and forth to thereby obtain uniform adhesion of the sealing foil to the microplate. It is also known to use heat-activated adhesives which require large heated stamps to fix the foils. Adhesive foils, however, often cause problems with respect to an air-tight sealing of the wells which can result in an undesired evaporation of fluids, thus impairing the reproducibility of test results. Especially in the case of small volume samples, variation between various reaction mixtures may occur.

Better results can be obtained using thermally fusible plastic foils. In practical use, the foil is positioned on top of the microplate and heated in order to soften and melt the foil at the interface between the plate and foil. While heated, the sealing foil is pressed on the microplate to ensure a close adhesive fit with full contact to the microplate. Once cooled, the foil acts as a leak proof seal on top of the microplate. Conventionally, a single piece of foil is cut to size and placed over the microplate, e.g., spanned in a frame. The foil is then pressed on the microplate, e.g., by manually or automatically holding a heated sealing stamp down. In automated instruments, a driving mechanism is used to bring the sealing stamp in and out of contact with the foil. It is also known to use a reel of foil which is automatically cut into sections during operation normally used in situations where a number of microplates need to be sealed automatically.

SUMMARY

In light of the foregoing, an improved instrument and method for processing liquid samples enabling sealing of microplates are disclosed. In one embodiment, an instrument for the automated storing and/or processing of liquid samples is disclosed. The instrument may comprise an instrument casing forming an internal space, a moving mechanism for moving at least one microplate for receiving the samples into or out of the internal space, and/or at least one rotatable sealing roller for pressing a sealing cover on the microplate while moving the microplate into or out of the internal space.

In another embodiment, a process for the automated storing and/or processing of liquid samples is disclosed. The process may comprise providing a microplate for receiving the samples, placing a sealing cover over the microplate, moving the microplate into or out of an internal space formed by an instrument casing, and/or pressing the sealing cover on the microplate while moving the microplate so as to fix the sealing cover to the microplate.

These and further features and advantages of the various embodiments of the invention will appear more fully from the following description, and the accompanying drawings.

REFERENCE LIST

Figure 1:
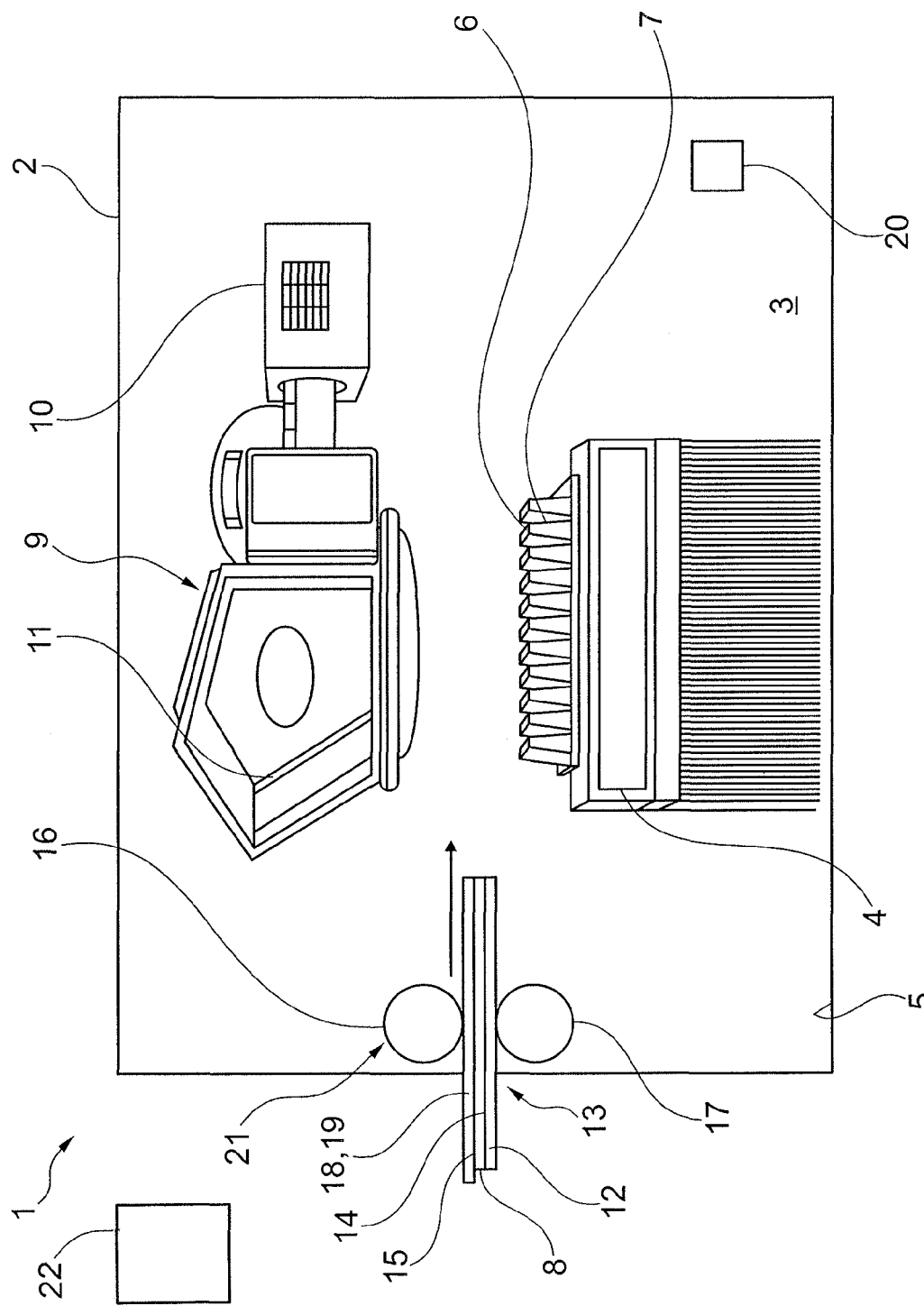
FIG. 1 is a schematic perspective view of an exemplary instrument according to an embodiment of the invention.

1 Instrument
2 Casing
3 Internal space
4 Block
5 Base
6 Seat
7 Recess
8 Microplate
9 Detection arrangement
10 Detector
11 Light guiding element
12 Tray
13 Tray port
14 Upper tray face
15 Upper plate face
16 Sealing roller
17 Supporting roller
18 Sealing cover
19 Frame
20 Controller
21 Moving mechanism
22 Feeding mechanism

DETAILED DESCRIPTION

By way of illustration, specific exemplary embodiments in which the invention may be practiced now are described. In this regard, terminology with respect to orientations and directions such as "horizontal", "vertical", "over", "under" is used with reference to the orientation of the figure being described. Because components of the exemplary instrument described can be positioned in a number of different orientations, this terminology is used for the purpose of illustration only and is in no way limiting.

According to an embodiment of the invention, a new instrument for the automated storing and/or processing of liquid samples is disclosed. The instrument can be configured in various ways in accordance with the specific demands of the user. In some embodiments, the instrument may be an instrument for incubating, thermally treating or otherwise processing liquid samples such as an automated thermocycler enabling liquid reaction mixtures to be put through a series of temperature excursions, e.g., for performing the PCR or any other reaction of the nucleic acid amplification type. In some embodiments, the instrument may be used for physically processing liquid samples, e.g., by centrifuging or shaking the liquid samples. In some embodiments, the instrument may be used for chemically processing liquid samples, e.g., by performing tests or assays related to immunochemical or clinical-chemical analysis items.

According to another embodiment of the invention, the instrument may include an instrument casing forming an internal space adapted for storing and/or processing liquid samples. In some embodiments, the internal space accommodates at least one processing device for processing liquid samples. In some embodiments, the processing device may be a physical processing device for physically processing the liquid samples such as a centrifuge or shaker. In some embodiments, the processing device may be a temperature-controlled member adapted for heating and/or cooling liquid samples for performing tests or assays with respect to clinical chemical or immunochemical analysis items, e.g., for melting nucleic acids or for performing the polymerase chain reaction or any other reaction of the nucleic acid amplification type. In some embodiments the temperature-controlled member may include one or more thermoelectric devices based on the Peltier effect. It is to be appreciated that when passing an electric current through a Peltier device, depending on the direction of current applied, the Peltier device functions as heat sink which absorbs heat or as heat source which releases heat to thereby cool or heat the temperature-controlled member.

The instrument may further include a moving mechanism for moving at least one microplate for receiving the samples into and/or out of the internal space. Specifically, in some embodiments, the moving mechanism may be adapted to move the microplate into an internal microplate position in the internal space for storing and/or processing liquid samples by the processing device. The microplate typically has an upper surface and an opposing lower surface wherein a plurality of open-top retention regions or wells sized to receive liquid samples is formed in the upper surface. In some embodiments, in which the processing device is a temperature-controlled member adapted for heating and/or cooling liquid samples, the internal microplate position enables a thermal communication between the microplate and the temperature-controlled member so as to thermally process the liquid samples contained therein.

In still other embodiments, the instrument may further include at least one rotatable sealing roller adapted for pressing a sealing cover for sealing the wells placed over the microplate on the microplate while moving the tray into or out of the internal space of the instrument so as to fix the sealing cover to the microplate. In some embodiments, the sealing roller may be rotatably mounted to a base of the instrument. In some embodiments, the sealing roller may be operatively coupled to a biasing member for biasing the sealing roller against the microplate so as to generate a pressing force to press the sealing cover on the microplate. In some embodiments, the sealing roller can be brought in and out of physical contact with the sealing cover, e.g., by means of an automated roller transport mechanism. In some embodiments, the sealing roller may be adapted for pressing the sealing cover on the microplate while moving the tray into the internal microplate position for storing and/or processing liquid samples.

In some embodiments, the instrument may further comprise a controller set up to control an automated sealing of the microplate, e.g., prior to storing and/or processing liquid samples.

In various embodiments, the instrument enables sealing of the wells of the microplate while the microplate is moved into or out of the internal space formed by the instrument casing for storing and/or processing liquid samples. Accordingly, a synergy is achieved as the transport of a microplate into the instrument casing is also used for fixing the sealing cover to the microplate for sealing the wells.

By providing in the various embodiments the integrated functionality of sealing the microplate combined with storing and/or processing liquid samples, the workflow for storing and/or processing liquid samples can be improved by saving time and costs. Otherwise, complexity of the total workflow is reduced.

The instrument and process according to embodiments of the present invention may further provide a facilitated loading of the instrument with a microplate as a user only needs to feed a microplate to the sealer. By using such a loading from the outside of the instrument casing to the sealer which transports the microplate into the instrument casing, the footprint of the instrument can be reduced.

In some embodiments, the moving mechanism may comprise a tray for holding the microplate which is movable into and/or out of the internal space formed by the instrument casing. Specifically, the tray can be movable between the internal microplate position and an external microplate position outside the instrument casing for loading and/or unloading the microplate to/from the tray. Specifically, in some embodiments, the tray may be movably mounted to a base for performing a repetitive, bidirectional movement between the internal and external microplate positions. In some embodiments, the moving mechanism may be configured as tray driving mechanism for driving the tray in either of the two directions, that is to say, for driving the tray into the internal and external microplate positions, respectively. In some embodiments, the internal space accommodates the at least one sealing roller. In some embodiments, the instrument casing may be a closed casing provided with a tray opening for transporting the tray into or out of the internal space. In some embodiments of the instrument of the invention, the tray may be provided with one or more resilient elements such as compression springs acting on the microplate so as to counteract the pressing force of the sealing roller. Accordingly, a full contact of the sealing cover with close fit to the microplate even in case of a slightly non-planar microplate can be obtained. In some embodiments, the microplate may be made of plastic material having a plate height of a few millimeters so that the microplate has sufficient flexibility to be planarized.

In some embodiments, the instrument may further include at least one rotatable supporting roller for supporting the microplate in a manner to counteract pressing action of the sealing roller so that the sealing cover can strongly be pressed on the microplate without exerting excessive load to the microplate. In some embodiments, the supporting roller may be rotatably mounted to a base.

In some embodiments, the instrument may further include a heating member for heating the at least one sealing roller so as enable heat transfer to the sealing cover while the sealing cover is pressed on the microplate. In some embodiments, the heating member may be adapted for generating Ohmic heat. Hence, the sealing cover can be softened and melt in the interface between the sealing cover and microplate so as to thermally fix the sealing cover to the microplate.

In some embodiments, the instrument may further include an automated feeding member, e.g. a reel of foil which can automatically be cut into sections during operation, for feeding the sealing cover upstream to the sealing roller while the microplate is moved into or out of the internal space. Accordingly, the sealing cover can readily be placed over the microplate while moving the microplate into or out of the internal space thus saving time for storing and/or processing liquid samples.

In some embodiments, the moving mechanism mentioned above may include the tray for holding the microplate which, in other embodiments, may be operatively coupled to a tray driving mechanism for moving the tray into and/or out of the internal space. In some embodiments, the moving mechanism, specifically the tray driving mechanism, may be a dedicated moving mechanism operatively coupled to the microplate and tray, respectively, for moving the microplate. In some embodiments, the moving mechanism may include the sealing roller, in which the sealing roller may be rotatably driven for moving the microplate. Specifically, in some embodiments, the sealing roller may be rotatably driven for moving the tray in either of the two directions. Hence, the sealing roller may not only be used for pressing the sealing cover on the microplate and, in some embodiments, for heating the sealing cover, but also for moving the microplate, e.g., by driving the tray. Providing the sealing roller with this double function, time and costs in processing liquid samples can be advantageously saved.

In some embodiments, the moving mechanism may include the supporting roller, in which the supporting roller may be rotatably driven for moving the microplate, e.g., by driving the tray in either of the two directions. Hence, the supporting roller may not only be used for counteracting the pressing force of the sealing roller but also for moving the microplate. Providing the supporting roller with this double function, time and costs in processing liquid samples can be advantageously saved.

According to another embodiment, a new process for the automated storing and/or processing of liquid samples is disclosed. The process may comprise one or more of the following:
  providing a microplate;
  placing a sealing cover over the microplate;
  moving the microplate into or out of an internal space formed by an instrument casing; in some embodiments, the microplate is moved in an internal microplate position adapted for storing and/or processing liquid samples; and
  pressing the sealing cover on the microplate while moving the microplate into or out of the internal space so as to fix the sealing cover to the microplate.

In some embodiments, the process may comprise moving a tray for holding the microplate in an external microplate position located outside the instrument casing and loading the microplate on the tray. In some embodiments, the process may comprise moving the tray from the external microplate position to the internal microplate position. In some embodiments of the process, the microplate may be automatically loaded or unloaded to/from the tray in the external microplate position so as to improve the workflow in storing and/or processing liquid samples.

In some embodiments of the process, the sealing cover may be heated while the sealing cover is pressed on the microplate so as to thermally fix the sealing cover to the microplate.

In some embodiments of the process, the sealing cover may be placed over the microplate while the microplate, e.g. held by the tray, is moved to the internal microplate position so as to improve the workflow by saving time for storing and/or processing liquid samples.

In some embodiments of the process, the tray may be uniformly moved while the sealing cover is heated and pressed on the microplate in order to uniformly transfer heat to liquid samples contained in the wells.

In some embodiments of the process, the sealing cover may be automatically placed over the microplate while the tray is moved into the internal microplate position so as to save time in storing and/or processing liquid samples.

In some embodiments of the process, the sealing cover-sealed microplate can be actively cooled in the internal microplate position so as to expedite cooling of the heated sealing cover and/or to cool liquid samples.

According to another embodiment, a new use for a driving roller for driving a tray for holding one or more microplates is disclosed. Accordingly, the driving roller may be used for pressing a sealing cover placed over a microplate on the microplate so as to fix the sealing cover to the microplate. In some embodiments, the driving roller may be used for heating the sealing cover so as to thermally fix the sealing cover to the microplate.

Referring now to FIG. 1, an instrument 1 having an integrated function of sealing microplates and cycling liquid reaction mixtures through a series of temperature excursions is illustrated. In some embodiments, the instrument 1 can be used for performing the PCR or any other reaction of the nucleic acid amplification type.

In some embodiments, the instrument 1 includes a closed casing 2 forming an internal space 3. With continued reference to the figure, in some embodiments, the internal space 3 accommodates a temperature-controlled block 4 placed on base 5 for heating and/or cooling the liquid reaction mixtures. In some embodiments, the base 5 is a locally fixed base. In some embodiments, the base 5 is a movable base. The temperature-controlled block 4 contains thermoelectric devices using the Peltier effect. Connected to a DC power source, each of the Peltier devices functions as a heat pump which can produce or absorb heat to thereby heat or cool the samples depending upon the direction of electric current applied. Accordingly, the temperature of the samples can be changed according to a predefined cycling protocol as specified by the user applying varying electric currents to the Peltier devices. It is to be appreciated that any other technique for heating and/or cooling the temperature-controlled block 4 can be used according to the specific demands of the user.

On its upper surface the temperature-controlled block 4 has a generally planar seat 6 for accommodating a microplate 8. The seat 6 is provided with a plurality of recesses 7 for receiving wells of the microplate 8 in close fit with full contact for thermal communication between the wells and the temperature-controlled block 4. As in line with terminology used in the introductory portion, the microplate 8 when placed on the seat 6 is in a processing position for thermally processing reagent mixtures contained therein.

Accordingly, the reaction mixtures contained in the microplate 8 can be thermally cycled through a series of temperature excursions. Specifically, in the PCR, a multiply repeated sequence of steps for the amplification of nucleic acids is done, wherein in each sequence the nucleic acids are melted (heat denaturated) to obtain denatured polynucleotide strands, primers are annealed to the denaturated polynucleotide strands, and the primers are extended to synthesize new polynucleotide strands along the denaturated strands to thereby obtain new copies of double-stranded nucleic acids. Due to the fact that reaction rates in the PCR-reactions vary with temperature, the samples are cycled through predefined temperature profiles in which specific temperatures are kept constant for selected time intervals. The temperature of the samples typically is raised to around 90° C. for melting the nucleic acids and lowered to approximately 40° C. to 70° C. for primer annealing and primer extension along the denaturated polynucleotide strands.

With continued reference to FIG. 1, in some embodiments, the instrument 1 includes a detection arrangement generally referred to at reference numeral 9 for optically detecting the reaction products of the amplification steps. Stated more particularly, the detection arrangement is positioned to detect emission beams emitted from the wells of the microplate 8 containing the reaction products. With yet continued reference to FIG. 1, in some embodiments, the detection arrangement 9 includes one or more detectors 10 for optically detecting the emitted light such as, but not limited to, charge coupled devices (CCDs), diode arrays, photomultiplier tube arrays, charge injection devices (CIDs), CMOS detectors and avalanche photo diodes. In some embodiments, the detection arrangement 9 also includes one or more excitation light sources such as lamps to excite emission of the emission beams from the reaction products. With yet continued reference to FIG. 1, in some embodiments, the detection arrangement 9 further includes light guiding elements 11 such as, but not limited to, lenses and mirrors and/or light separating elements such as, but not limited to, transmission gratings, reflective gratings and prisms. Specifically, radiation such as excitation light can be transmitted to the samples and (e.g. fluorescent) light emitted to the one or more detectors can be detected. Specifically, in the detection arrangement 9, the reaction products can also be detected during the progress of the reactions. Since the optical detection of reaction products is well-known to those of skill in the art, it is not further elucidated herein.

The instrument 1 further includes a tray 12 adapted for supporting the microplate 8 in horizontal position on upper tray face 14. With reference to FIG. 1, in some embodiments, the tray is slidably mounted to the base 5 enabling a repetitive, bidirectional movement between the processing position inside the casing 2 for thermally processing the reaction products and a loading position outside the casing 2 for loading or unloading the microplate 8 on/from the tray 12. In some embodiments, the tray 12 can be horizontally moved through a tray port 13 (not further detailed in FIG. 1). Since such sliding mechanism is well-known to those of skill in the art, it need not be further elucidated herein. In some embodiments, the instrument 1 includes an automated tray driving mechanism such as a motor-based belt- or wheel-drive for automatically moving the tray 12 between the processing and loading positions. Since such driving mechanism is well-known to those of skill in the art, it need not be further elucidated herein.

In some embodiments, an upper plate face 15 of the microplate 8 forms a plurality of open-top wells (not illustrated) for receiving reaction mixtures which typically include biological material with nucleic acids. The wells usually are regularly arranged in a two-dimensional array of columns and rows intersecting each other at right angles. In some embodiments, the microplate is an integrally molded plastic disposable intended for single use only.

While not illustrated in FIG. 1, in some embodiments, the tray 12 can, e.g., be provided with a plurality of resilient members in an upright position relative to the upper tray face 14 in parallel alignment with respect to each other. The resilient members can, e.g., be configured as helical compression springs. The resilient members can, e.g., be arranged in correspondence to the wells of the microplate 8 so that their number corresponds to the number of the wells. The resilient members can, e.g., be adapted to accommodate one well so that can be they can be elastically compressed between the tray 12 and the microplate 8.

With continued reference to FIG. 1, in some embodiments, the instrument 1 yet further includes one (upper) sealing roller 16 and one (lower) supporting 17, both of which are rotatably mounted to the base 5. The rollers 16, 17 are in opposite relationship with respect to each other keeping an inter-distance enabling the tray 12-held microplate 8 to pass in-between them. Specifically, the sealing roller 16 is arranged to press a sealing cover 18 placed on the upper plate face 15 on the microplate 8 wherein the supporting roller 17 is arranged to counteract the pressing force of the sealing roller 16.

In some embodiments, the sealing roller 16 is non-heated so as to fix the sealing cover 18 by pressure action to the microplate 8. In that case, the sealing cover 18 usually is provided with an adhesive backing facing the microplate 8. In some other embodiments, the sealing roller 16 is heated to simultaneously transfer heat to the sealing cover 18 while it is pressed on the microplate 8. In that case, the sealing cover 18 is thermally fusible to be thermally fixed to the microplate 8. By transferring heat to the sealing cover 18, the sealing cover 18 can be softened and melted so as to thermally fix it to the microplate. In some embodiments, the sealing roller 16 is spatially fixed with respect to the casing 2. In some other embodiments, the sealing roller 16 can actively be brought in and out of contact with the sealing cover 18, e.g., by vertically moving the sealing roller 16 by means of a transport mechanism which is not further detailed herein.

As illustrated in FIG. 1, in some embodiments, the sealing cover 18 is cut to size and spanned on a frame 19 to be readily placed on top of the microplate 8 adjacent the wells. As further illustrated in FIG. 1, in some embodiments, the sealing cover 18 is placed on the microplate 8 outside the casing 2.

In some alternative embodiments, the sealing cover 18, spanned on frame 19, is placed on the microplate 8 in the internal space 3 upstream of the sealing and supporting rollers 16, 17, respectively with respect to transporting the microplate 8 into processing position. In some other alternative embodiments, the sealing cover 18 is cut into sections from a reel of foil (not illustrated) and placed over the microplate 8 upstream of the sealing and supporting rollers 16, 17 inside the casing 2, respectively with respect to transporting the microplate 8 into processing position. In other embodiments, the instrument 1 may further include an automated feeding mechanism 22, e.g. providing the reel of foil, which can automatically cut the foil into sections during operation and automatically feed the cut foil (i.e., the sealing cover 18) upstream to the sealing and supporting rollers 16, 17 while the microplate 8 is moved into or out of the internal space 3. In still other embodiments, each cut section of the reel of foil which forms the sealing cover 18 can be placed over the microplate 8 either inside or outside the casing 2. Accordingly, the sealing cover 18 can readily be placed over the microplate 8 while moving the microplate into or out of the internal space 3 thus saving time for storing and/or processing liquid samples.

Bi-directionally driving the tray 12 into processing and loading positions, respectively, can be done by a dedicated tray driving mechanism (not illustrated) operatively coupled to the tray 12. In this case, the sealing roller 16 and/or the supporting roller 17 can be non-driven idle rollers. Additionally or alternatively, the sealing roller 16 and/or the supporting roller 17 can be driven and be adapted for driving the microplate 8 into processing and loading positions, respectively. Accordingly, the tray driving mechanism and/or the sealing roller 16 and/or the supporting roller 17 form a moving mechanism generally referred to at reference numeral 21 for moving the microplate 8 between the loading and processing positions.

The instrument 1 further includes a controller 20 set up to control sealing of the microplate 8. The controller 20 can, e.g., be embodied as programmable logic controller running a computer-readable program. The controller 20 is electrically connected to the instrument components which require control and/or which provide information which includes the temperature-controlled block 4, the detection arrangement 9 and, optionally when heated, the sealing roller 16.

In practical use, under control of the controller 20, in some embodiments, the tray 12 is horizontally moved through the tray port 13 into loading position outside the casing 2 where the microplate 8 containing the reaction mixtures is placed on the tray 12. Furthermore, the frame-spanned sealing cover 18 is placed on the upper plate face 15 of the microplate 8 covering its wells containing the reaction mixtures. Placing of the microplate 8 and/or the sealing cover 18 can be done manually or automatically, e.g., by means of a robotic arm.

The tray 12, together with the microplate 8 and sealing cover 18 placed thereon, is then horizontally moved into processing position on the seat 6 of the temperature-controlled block inside the casing 2 where the microplate 8 is kept ready for thermal processing of the reaction products. While moving the tray 12 into processing position, the tray-held microplate 8 passes in-between the sealing and supporting rollers 16, 17. While passing, the sealing roller 16 presses the sealing cover 18 on the upper plate face 15 and simultaneously transfers heat to the sealing cover 18 for thermally fixing the sealing cover 18 to the microplate 8. While thermally fixing the sealing cover 18, the tray 12 is moved with highly constant speed so as to prevent the reaction mixtures from experiencing an undesired uneven heat transfer when transferring heat to the sealing cover 18.

Once, in processing position, the microplate is actively cooled to accelerate sealing of the wells and to reduce undesired thermal strain of the reaction mixtures. In processing position, thermal processing of the sealed reaction mixtures can be done as-above detailed detecting the reaction products obtained. Following nucleic acid amplification, the tray 12 is horizontally moved through the tray port 13 into loading position outside the casing 2 where the microplate 8 containing the reaction products is removed from the tray 12. Removal of the microplate 8 can be done manually or automatically, e.g., by means of a robotic arm.

Accordingly, in the instrument 1, the microplate 8 can be thermally sealed simultaneously with moving into processing position for processing the reaction mixtures contained. Hence, provided with an integrated sealing device, the workflow for processing the reaction mixtures is improved saving time and costs in performing the amplification steps.

Figure 2:
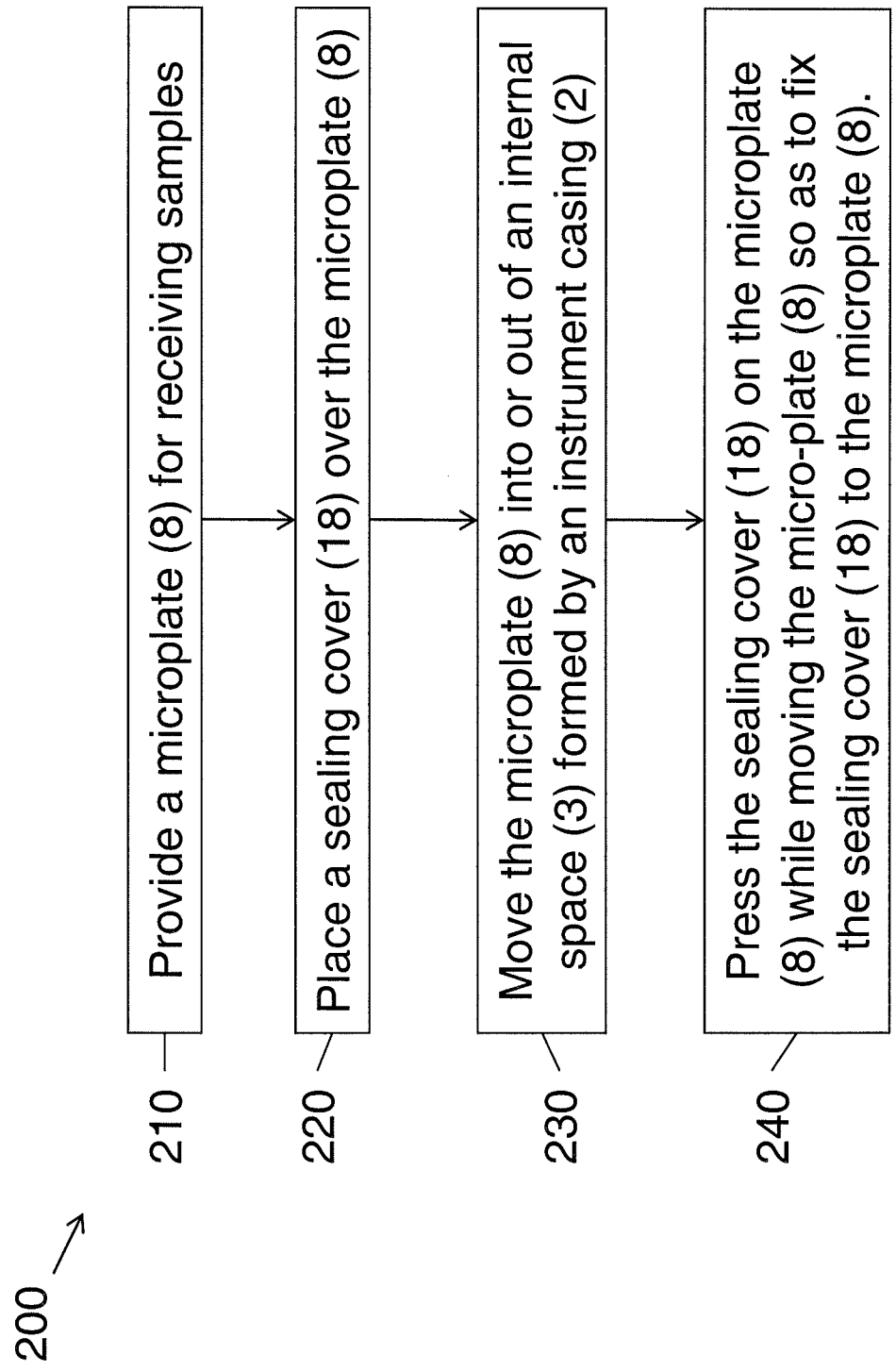
FIG. 2 is a flow chart of an exemplary process according to an embodiment of the invention.

With reference now made to the flow chart depicted by FIG. 2, a process for the automated storing and/or processing of liquid samples according to an illustrated embodiment is disclosed. The illustrated process 200 comprises providing a microplate 8 (FIG. 1) for receiving the liquid samples at block 210. Next, in block 220, the process 200 includes placing a sealing cover 18 over the microplate 8, and then in block 230, moving the microplate 8 into or out of an internal space 3 formed by an instrument casing 2. The process 200 further includes pressing the sealing cover 18 on the microplate 8 while moving the microplate 8 so as to fix the sealing cover 18 to the microplate 8 in block 240. In other embodiments of the process 200, the sealing cover 18 may be heated while the sealing cover 18 is pressed on the microplate 8 so as to thermally fix the sealing cover 18 to the microplate 8 in block 240. In still other embodiments of the process 200, the sealing cover 18 may be placed over the microplate 8 in block 220 while the microplate 8 is moved into or out of the internal space 3 in block 230. Yet in other embodiments of the process 200, the microplate 8 may be automatically loaded or unloaded to/from a tray 12 in block 210. In other embodiments of the process 200, the sealing cover 18 may be automatically placed over the microplate 8 in block 220 while the microplate 8 is moved into or out of the internal space 3 in block 230. In still other embodiments, the sealing cover-sealed microplate 8 may be actively cooled in the internal space 3 in block 230. It is to be appreciated that one or more of the above mention process steps of the process 200 may be performed automatically under the control of the controller 20 in still further embodiments. It is further to be appreciated that although the process steps depicted by blocks 210-240 are shown as being performed sequentially, some of the processes may be performed in parallel in still other embodiments.

Obviously many modifications and variations of the present invention are possible in light of the above description. It is therefore to be understood, that within the scope of appended claims, the invention may be practiced otherwise than as specifically devised.

What is claimed is:

1. An instrument for the automated storing and/or processing of liquid samples, comprising: an instrument casing forming an internal space; at least one liquid sample chemical processor for chemically treating the liquid sample and at least one liquid sample thermal processor for thermally treating the liquid sample contained within the internal space; a moving mechanism for moving at least one microplate for receiving said samples into or out of said internal space; at least one rotatable sealing roller for pressing a sealing cover on said microplate while moving said microplate into or out of said internal space.

2. The instrument according to claim 1, further comprising at least one rotatable supporting roller for supporting said microplate in a manner to counteract pressing of said sealing roller.

3. The instrument according to claim 1, wherein said sealing roller can be heated so as to transfer heat to said sealing cover while pressing said sealing cover on said microplate.

4. The instrument according to claim 1, wherein said sealing roller is operatively coupled to a biasing member for biasing said sealing roller against said microplate.

5. The instrument according to claim 1, further including an automated feeding mechanism for feeding said sealing cover upstream to said sealing roller while moving said microplate into or out of said internal space.

6. The instrument according to claim 1, wherein said moving mechanism comprises said sealing roller, said sealing roller being rotatably driven for moving said microplate into our out of said internal space.

7. The instrument according to claim 2, wherein said moving mechanism comprises said supporting roller, said supporting roller being rotatably driven for moving said microplate into our out of said internal space.

8. The instrument according to claim 1, wherein said moving mechanism comprises a tray for holding said microplate, said tray being movable into or out of said internal space.

9. The instrument according to claim 8, wherein said tray can be moved in an external position for loading or unloading said microplate to and from said tray located outside said instrument casing.

10. A process for the automated storing and/or processing of liquid samples, comprising: providing a microplate for receiving said samples; placing a sealing cover over said microplate; moving said microplate into or out of an internal space formed by an instrument casing, the internal space comprising at least one liquid sample chemical processor for chemically treating the liquid sample and at least one liquid sample thermal processor for thermally treating the liquid sample; pressing said sealing cover on said microplate while moving said microplate so as to fix said sealing cover to said microplate; and processing the samples by the at least one liquid sample chemical processor and the at least one liquid sample thermal processor.

11. The process according to claim 10, wherein said sealing cover is heated while said sealing cover is pressed on said microplate so as to thermally fix said sealing cover to said microplate.

12. The process according to claim 10, wherein said sealing cover is placed over said microplate while said microplate is moved into or out of said internal space.

13. The process according to claim 10, wherein said microplate is automatically loaded or unloaded to and from a tray.

14. The process according to claim 10, wherein said sealing cover is automatically placed over said microplate while said microplate is moved into or out of said internal space.

15. The process according to claim 10, wherein said sealing cover-sealed microplate is actively cooled in said internal space.

16. An instrument for the automated storing and/or processing of liquid samples, comprising: an instrument casing forming an internal space; at least one liquid sample chemical processor for chemically treating the liquid sample, and at least one liquid sample thermal processor for thermally treating the liquid sample, said chemical processor and thermal processor contained within the internal space; a moving mechanism for moving at least one microplate for receiving said samples into or out of said internal space; at least one rotatable sealing roller for pressing a sealing cover on said microplate while moving said microplate into or out of said internal space.

17. The instrument for automated storing and/or processing of liquid samples according to claim 16 wherein the thermal processor is configured for thermal cycling of the liquid sample.

* * * * *